United States Patent [19]

Nadolsky

[11] Patent Number: 4,978,781

[45] **Date of Patent: * Dec. 18, 1990**

[54] LOW-FOAM ALKALI-STABLE AMPHOTERIC SURFACE ACTIVE AGENTS

[75] Inventor: Richard J. Nadolsky, Plainsboro, N.J.

[73] Assignee: Miranol, Inc., Dayton, N.J.

[ * ] Notice: The portion of the term of this patent subsequent to Jan. 2, 2007 has been disclaimed.

[21] Appl. No.: 412,274

[22] Filed: Sep. 25, 1989

Related U.S. Application Data

[62] Division of Ser. No. 901,268, Aug. 27, 1986, Pat. No. 4,891,159.

[51] Int. Cl.$^5$ .................. C07C 303/00; C07D 279/12

[52] U.S. Cl. .................................... 562/102; 562/43; 544/59; 544/159

[58] Field of Search .......................... 562/44, 102, 43; 544/59, 159

[56] References Cited

U.S. PATENT DOCUMENTS 4,891,159 1/1990 Nadolsky .......................... 562/102

*Primary Examiner*—Alan Siegel
*Attorney, Agent, or Firm*—Ladas & Parry

[57] ABSTRACT

The present invention relates to low-foam alkali-stable surface active agents which are amphoteric. The subject materials are hydroxypropyl sultaines.

11 Claims, No Drawings

LOW-FOAM ALKALI-STABLE AMPHOTERIC SURFACE ACTIVE AGENTS

This application is divided out of co-pending application 06/901,268, filed on Aug. 27, 1986, now U.S. Pat. No. 4,891,159.

BACKGROUND OF THE INVENTION

U.S. Pat. No. 2,198,822 describes certain amphoteric shampoo materials including products of the formula:

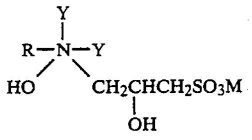

wherein R is a hydrocarbon radical of 6–24 carbon atoms, Y is aliphatic hydrocarbon of 1–6 carbons or $-R^1-O(R^1O)_xH$ wherein $R^1$ is alkylene of 2–4 carbons and x is 0–15 and M is hydrogen, sodium, potassium or other alkali metal.

These products are not stated to have any stability in strong alkali. Also, U.S. Pat. No. 2,168,538 describes certain amide derivatives of the general formula:

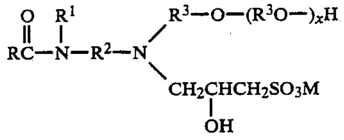

wherein R is hydrocarbon of 4 to 18 carbon atoms, $R^3$ is alkylene of 2 to 4 carbons, $R^2$ is alkylene or hydroxy alkylene of 2 to 6 carbon atoms or an alkylene oxide adduct thereof and $R^1$ is hydrogen, alkyl, hydroxy alkyl or an alkylene oxide adduct thereof, M is hydrogen or an alkali metal. Reference is made to possible quaternized oligomers of these compounds but there is no exemplification of such products.

These products also are not stated to possess any special stability toward alkali.

U.S. Pat. No. 4,246,194 (Ferguson assigned to Research Organics Inc. issued January 20, I98l) discloses compounds inter alia of the formula:

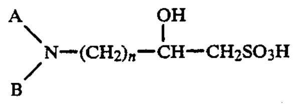

wherein A and B are each hydrogen, aliphatic, cycloaliphatic or hydroxyaliphatic and n is 1 or 2. The compounds are stated to be useful as hydrogen ion buffers in a desirable pKa range for biological research. No suggestion is made that the products should be quaternized. Nor is there any suggestion that quaternized products would be useful.

The need for surface active agents that are stable in moderately strong alkali is discussed in U.S. Pat. No. 4,214,102. This patent teaches that the presence of an amide linkage destablizes many materials in strong acids and strong alkalies since this linkage readily breaks down in such media resulting in turbid solutions. The objective of the invention described therein is said to be "the development of amphoteric surface-active compounds which are stable over a wide pH range from acidic to alkaline over long periods of time and which have at least three hydroxyl and/or ether groups to give a greater hydrophilic effect to the molecule". The products are obtained by reaction of a glycidyl ether with an excess of an N-hydroxy-$C_{2-4}$-alkyl-$C_{2-6}$-alkylene diamine and then N-alkylating the product with an excess of halo $C_{2-4}$ alkanoic acid or halo $C_{2-4}$ hydroxyalkane sulfonic acid. Among the compounds produced are ones that have "the probable formulae":

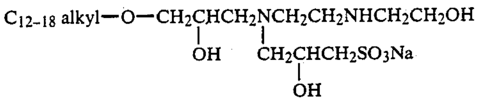

and

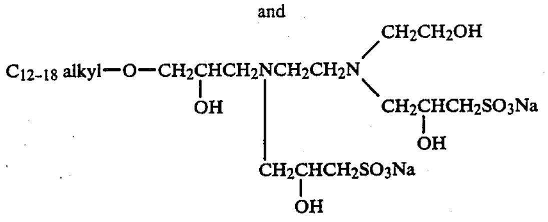

The products formed are shown to be good foamers and stable in either 20% NaOH or 20% $H_2SO_4$. However, the surface tension of 20% NaOH containing either 1% or 5% of the subject product was only reduced to 66.4 dyne/cm indicating very poor surface activity in such a solution.

Alkylamino sulfonic acids are also described in U.S. Pat. Nos. 4,481,150; 4,138,345; 3,998,796; 3,075,899;and 1,994,300. None of these claim any particular alkali stability for the products disclosed.

Zielinska (Chemical Abstracts 104:209 195 c describes surfactants of the formula $$ROCH_2CH(OH)CH_2N^{\oplus}R'_2CH_2CH(OH)CH_2SO_3^{\ominus}$$

that are prepared by reaction of compounds of the formula $$ROCH_2CH(OH)CH_2NR'_2 \text{ or } RNHCH_2CH_2NR'_2$$

with epichlorohydrin and sodium sulfite. They are stated to have good detergent and bactericidal properties.

There has long been a need for alkali-stable surface active agents. The only product currently on the market that is stable in concentrated alkali (30–50% solutions of NaOH) is that sold under the trademark Triton BG-10. This product is comprised of higher alkyl monosaccharides and higher alkyl oligosaccharides of the type described in U.S. Pat. No. 3,839,318. Triton BG-10 has several shortcomings: it is quite dark, viscous, has a burnt odor, only slowly dissolves in 50% NaOH, does not reduce the surface tension of 50% NaOH to any great extent, and produces considerable foam as well.

It is an object of the present invention to produce materials that are compatible with aqueous solutions of NaOH containing up to 50% NaOH. It is a further object of this invention to produce materials that dissolve readily in concentrated aqueous NaOH and that appreciably reduce the surface tension of such solutions. A further object is to produce materials that will remain dissolved when concentrated NaOH containing these materials is diluted with water to normal use concentrations of 5–20% NaOH and will significantly lower the surface tension of such solutions. A further object is to produce materials that will generate little or no foam in solutions containing 50% or less NaOH. Still a further object of the present invention is to produce materials that will remain unchanged in solutions containing 5–20% NaOH upon extended boiling of such solutions.

These and other objects are achieved by use of materials of the general formula:

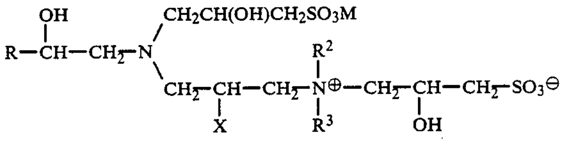

wherein R is selected from alkyl, aryl, or alkylaryl groups of 4–18 carbon atoms or alkoxymethylene wherein the alkoxy group contains 4–18 carbon atoms. $R^2$ and $R^3$ are individually selected from the group consisting of methyl; alkyl of 2–6 carbon atoms, where said alkyl group is substituted by an electron-donating group on the beta carbon atom thereof; polyoxyethylene and polyoxypropylene. Alternatively, $R^2$ and $R^3$ may together be $—CH_2CH_2OCH_2CH_2—$ or $—CH_2CH_2SCH_2\ CH_2—$ (i.e. together with nitrogen constitute a morpholine or thiomorpholine ring).

M is hydrogen or an alkali metal cation; and X is hydrogen or an electron-donating group such as OH, SH, $CH_3O$ or $CH_3S$.

Typically the R group contains 4–14, commonly 4–8 carbon atoms. Preferably, R is alkoxymethylene containing 4–8 carbon atoms in the alkoxy group such as butoxymethylene, hexyloxymethylene, 2-ethylhexyloxymethylene. $R^2$ and $R^3$ are each preferably methyl, hydroxyethyl, 2-hydroxypropyl, or together, and with the nitrogen atom to which they are bound, form a morpholine ring. X is preferably hydrogen.

Without wishing to be bound by any theory, it is believed that the alkali stability of the products of the present invention derives from the general provision of electron-donating groups on carbon atoms in positions beta to quaternary nitrogen. Such groups make the hydrogens of beta carbon atoms less acidic and thereby counteract degradative processes such as those described by Hofmann (Ber., 14, 659 (1881). Typically such groups include hydroxy, alkoxy, mercapto, and alkylthio. Suitable alkoxy and alklythio groups contain 1–4 carbon atoms.

The products of the present invention are prepared by alkylation of a compound of the formula:

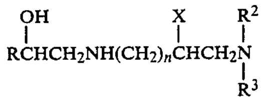

(3)

with an alkylating agent of the formula:

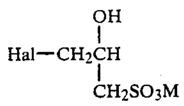

where Hal is halogen, typically chlorine and M is an alkali metal cation, typically sodium.

DETAILED DESCRIPTION OF THE INVENTION

Intermediate amino compound (3) is prepared by reaction of a disubstituted aminoalkyl primary amine with a suitable 1,2-epoxyalkane or, more preferably, with a suitable alkylglycidyl ether. Suitable amines include 3-dimethylaminopropylamine, 3-bis (2- hydroxyethyl) aminopropylamine, and 2- bis (2-hydroxyethyl) amino- ethylamine. This reaction may be run with or without a solvent and at a temperature generally ranging from 20–100° C. The reaction is often exothermic and the temperature may be controlled by the addition of a solvent or by controlling the rate of addition of the epoxide to the amine or amine solution. Even lower temperatures may be employed for this reaction, but then reaction times must be extended. The choice of solvent and of temperature for this reaction is largely dependent on which starting amine is used More critical to the production of a suitable intermediate is the molar ratio of starting amine to epoxide. With disubstituted aminoalkyl primary amines, a molar excess of amine to epoxide generally within the range 1.5–2.0:1.0 is used. This excess minimizes the formation of dialkylation product of the structure:

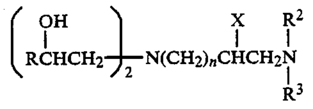

When excess amine is employed in making the intermediate product, it is removed from this product before further reaction. This is usually accomplished by distillation, employing vacuum if necessary. However, other suitable methods such as solvent extraction may also be used to remove excess amine.

The second stage, alkylation with alkali metal salt of 3-halo-2-hydroxypropanesulfonic acid, is typically carried out at an elevated temperature, frequently between 50 and 100° C, in an aqueous environment. The most commonly used alkylating agent is the sodium salt of 3-chloro-2-hydroxypropane sulfonic acid. This is obtained by reaction of epichlorohydrin with sodium metabisulfite in water by methods well known to those skilled in the art. It may be desirable to mix the alkylating agent and amino intermediate at a temperature in the range 55–60° C. and then raise this temperature after the initial admixture is complete, for example, to a temperature in the range 85–95° C. An alkaline pH will normally be maintained during the alkylation, for example, in the range 8.0–9.0. This is normally accomplished by the incremental addition of sodium hydroxide (usually a 25–50% solution).

The products of the present invention find a variety of uses. Typically, they are incorporated in cleaning and similar compositions having a relatively high alkali content, for example, in the range 5–50% sodium or potassium hydroxide or equivalent such as strong sodium carbonate solutions. Such compositions include formulations for produce peeling, hard-surface cleaners, oven cleaners, wax strippers, degreasers, aluminum cleaners, bottle washing formulations and, when the caustic content is at the lower end of the range, these products may be used in laundry and dishwashing detergents, hand cleansers, and concentrates for producing such cleaners.

Compounds typically present in such formulations include those produced by the illustrative examples which are believed to be predominantly of the formulae;

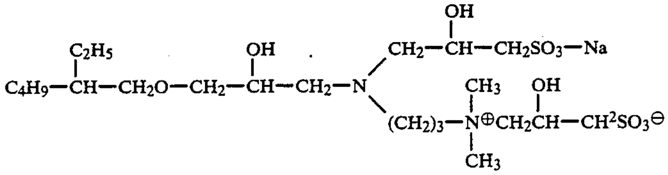

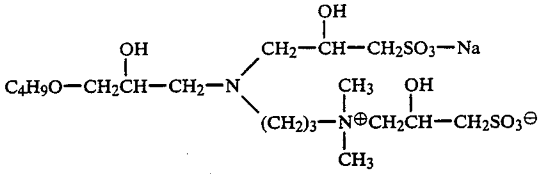

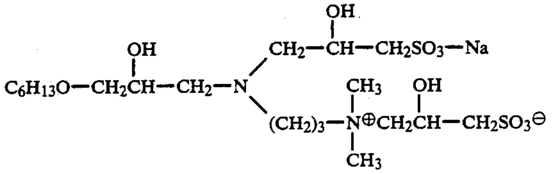

and

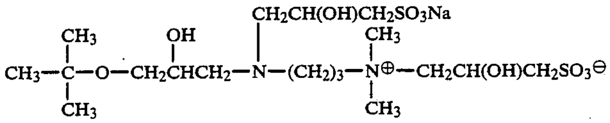

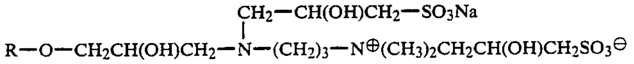

wherein R represents the residue of a lauryl myristyl alcohol mixture.

Such formulations may also contain conventional additives therefor including silicates, phosphates, pyrophosphates and polyphosphates for example in the form of the sodium salts. Other additives that may be present include lower alcohols of 1–6 carbons, glycols, glycol ethers, chelating agents, thickeners such as amides, cellulose derivatives and polyacrylates. In some cases, additional anionic, nonionic or amphoteric surface active agents may also be present.

Typically, the products of the present invention will be present in amounts of from 0.1 to 10 percent by weight of a formulation as used. Concentrates which are to be diluted will generally contain higher percentages (within this range) of products of the present invention. Blends of various individual products of the present invention will frequently optimize several of the stated objects of this invention better than any single product.

This invention will now be illustrated by the following Examples:

EXAMPLE I

Part A. Amine-Epoxide Reaction

3-Dimethylaminopropylamine (204g, 2.0 moles) was added to a reaction flask equipped with a mechanical stirrer, reflux condenser, thermometer, and addition funnel While stirring, the amine was heated to 90–100° C. To this was added 2-ethylhexyl glycidyl ether (186g, 1.0 mole) at such a rate as to maintain a reaction temperature of 90–100°C. without supplying heat. Addition time was about 1 hour. The reaction mixture was stirred for an additional period at 90–100°C. until reaction was complete as judged by the disappearance of epoxide absorbances at 50, 915, and 1250 $cm^{-1}$. When reaction was complete, vacuum was applied to strip out unreacted 3-dimethylaminopropylamine. The product had a neutralization equivalent (NE) of 157 (theoretical NE=144 for a 1:1 adduct).

Part B. Alkylation with Sodium-3-Chloro2-Hydroxypropane Sulfonate

The title alkylating agent was made by reacting sodium metabisulfite (104.5g) with epichlorohydrin (101.8g) in water (481g). To this solution of alkylating agent at 50–60° C. was added the product from Part A (157g). This mixture was stirred and heated to 85–90° C. Reaction was continued with the pH maintained in the range 8 to 9 by the incremental addition of 50% aqueous NaOH. Reaction was continued until the pH had stabilized and the ratio of ionic chloride to total chloride exceeded 0.99. Vacuum was applied to remove water until sufficient water had been removed to give a 50% solids product which was a clear, yellow liquid.

EXAMPLE II

Part A. Amine-Epoxide Reaction

The same procedure was used as for Example IA except butyl glycidyl ether (130g, 1.0 mole) was used with 3-dimethylaminopropyl amine (204g, 2.0 moles).

The product's measured NE was 125 (theoretical NE=116 for a 1:1 adduct)

Part B-1. Alkylation

The same procedure was used as in Example IB except that 125g of product IIA was added instead of the 157g of product IA. After completion and vacuum stripping to 50% solids, the product obtained was a clear, yellow liquid.

Part B-2. Alkylation

The same procedure was used as for Example IIB-1, except that only one-half the amounts of sodium metabisulfite and epichlorohydrin were employed The product, at 50% solids was a clear, light yellow liquid.

EXAMPLE III

PART A. HEXYL GLYCIDYL ETHER/HEXYL CHLOROHYDRIN ETHER

To a reaction flask equipped with a mechanical stirrer, reflux condenser, thermometer, and addition funnel was added n-hexyl alcohol (357g, 3.5 moles) along with 9g of boron trifluoride in methanol (10–15% $BF_3$).

This mixture was stirred and heated to 90–100° C. Epichlorohydrin (92.5g, 1.0 mole) was added at such a rate as to maintain 90–100° C. Addition time was about 1 hour. Reaction was complete after about 2 more hours at this temperature as judged by virtual disappearance of epoxide absorbances at about 850, 915 and 1250 $cm^{-1}$. The excess hexyl alcohol was stripped off at 55–60° C and 10 mm Hg vacuum. The product was distilled at 10 mm Hg removing as a forerun material boiling below 120° C The product was collected at 120–125° C/10 mm Hg. Analysis indicated that distillate consisted of approximately 20% hexyl glycidyl ether and 80% of 3-chloro-2-hydroxypropyl hexyl ether.

Part B. Reaction with Amine

The distillate from Part A (192.5g) was added to 3-dimethylaminopropyl amine (153g, 1.5 moles) at 90–100° C at such a rate as to maintain that temperature without supplying heat. Addition time was about 1 hour. After an additional 3 hours at 90–100° C., the ratio of ionic chloride to total chloride was greater than 0.99. Temperature was maintained in this range for 1 more hour until the typical epoxide absorbances had disappeared, then unreacted amine was removed at a temperature up to 120° C. at 5–10 mm Hg. To the remaining material was added 88g of 50% aqueous NaOH plus sufficient water (about 150 cc) to dissolve the salt that formed. The aqueous phase was removed and the product washed twice with saturated salt solution. The product's NE was 177.6 (theoretical NE=130 for a 1:1:1).

Part C. Alkylation

The same procedure was used as in Example IB except that 177.6g of product III B was added instead of 157g of product IA and the amount of water was adjusted to give a 36% solids product.

EXAMPLE IV

An identical procedure was used as for Example II (Part A and Part Bl) except that t-butyl glycidyl ether was added instead of butyl glycidyl ether and the final product (IV-B) was adjusted to 50% solids.

COMPARATIVE EXAMPLE Part A.

Amine-Epoxide Reaction

The same procedure was used as for Example IA except aminoethylethanol amine (208g, 2.0 moles) was used in place of dimethylaminopropyl amine. When reaction was complete, the separated product's NE measured 149.8 (theoretical NE=145 for a 1:1 adduct).

Part B. Alkylation

The same procedure was used as for Example IB, except that 149.8g of product from Part A of this Example was added instead of 157g of product IA and the solids were adjusted to 30%. The product of this Comparative Example is similar to that of Example II of Leender's U.S. Pat. No. 4,214,102.

The stability of the products of the present invention in aqueous sodium hydroxide is shown by the following table:

| | In 50% NaOH | | In 10% NaOH | |
|---|---|---|---|---|
| Product | Amount[1] | Surface[2] Tension | Amount[1] | Surface[2] Tension |
| IB | 0.75 | 85.5 (cloudy) | 0.15 | 27.2 |
| IIB-1 | 0.75 | 58.3 | 0.15 | 35.7 |
| IIB-2 | 0.75 | Insoluble | 0.75 | 28.8 (cloudy) |
| IIIC | 0.75 | 64.2 | 0.15 | 26.1 |
| IVB | 0.75 | 64.0 | 0.15 | 48.3 |
| 50% IB/50% IVB | 0.75 | 60.6 | 0.15 | 26.6 |
| Comparative | 0.75 | Insoluble | 0.15 | 29.9 |

[1]Represents grams of product solids/100 grams caustic solution
[2]In dyes/cm

All products above, with the exception of those noted as insoluble remained dissolved in the 50% NaOH for at least 1 week. Several samples exhibited no change in appearance or in surface tension even after 1 month. For all products in 10% NaOH, boiling for 16 hours had no appreciable effect on the measured surface tension.

I claim:

1. Surface active compound of the formula:

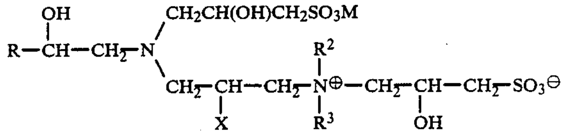

wherein

R is selected from the group consisting of alkyl, aryl, alkylaryl groups of 4–18 carbons and alkoxymethylene wherein the alkoxy group is of 4–18 carbon atoms, $R^2$ and $R^3$ are individually selected from the group consisting of methyl; alkyl of 5 to 6 carbon atoms wherein said alkyl group is substituted by an electron-donating group selected from the group consisting of OH, SH, $CH_3O$ and $CH_3S$ on the beta carbon atoms thereof; polyoxyethylene and polyoxypropylene or $R^2$ and $R^3$ may jointly form a $CH_2CH_2OCH_2CH_2$ or $CH_2CH_2SCH_2CH_2$ groups so as to form, together with the nitrogen atom to which they are bound, a morpholine or thiomorpholine ring, M is hydrogen or an alkali metal cation; X is hydrogen or an electron-donating group selected from the group consisting of OH, SH, $CH_3O$ and $CH_3S$.

2. A surface active compound according to claim 1 wherein $R^2$ is methyl.

3. A surface active compound according to claim 1 wherein $R^3$ is methyl.

4. A surface active compound according to claim 1 wherein both $R^2$ and $R^3$ are methyl.

5. A surface active compound according to claim 4 wherein R is an alkyl group containing from 4–14 carbon atoms.

6. A surface active compound according to claim 5 wherein R is alkoxy methylene of 4–8 carbon atoms in the alkoxy group.

7. A compound according to claim 1

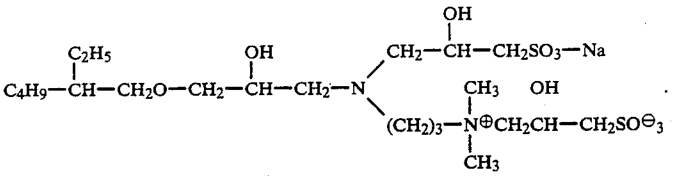

8. A compound according to claim 1

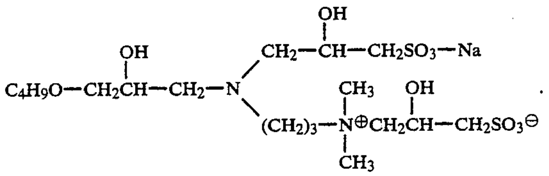

9. A compound according to claim 1

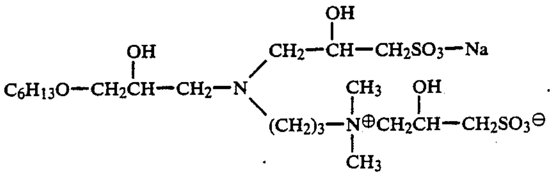

10. A compound according to claim 1

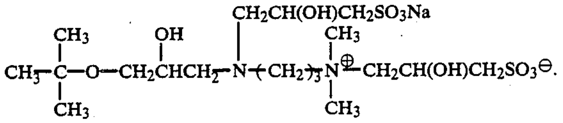

11. A compound according to claim 1

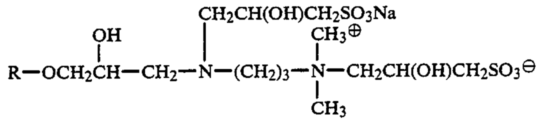

wherein R represents a mixture of lauryl and myristyl groups.

* * * * *